US00PP15479P2

(12) United States Plant Patent
Eggleton

(10) Patent No.: US PP15,479 P2
(45) Date of Patent: Jan. 11, 2005

(54) ***GAURA* PLANT NAMED 'BIJOU BUTTERFLIES'**

(50) Latin Name: *Gaura lindheimeri*
Varietal Denomination: Bijou Butterflies

(76) Inventor: Steven Eggleton, 3 Harris Road, Wonga Park, Melbourne, Vic (AU), 3115

( * ) Notice: Subject to any disclaimer, the term of this patent is extended or adjusted under 35 U.S.C. 154(b) by 0 days.

(21) Appl. No.: 10/676,193

(22) Filed: Sep. 30, 2003

(51) Int. Cl.[7] ..... A01H 5/00
(52) U.S. Cl. ..... Plt./226
(58) Field of Search ..... Plt./226

*Primary Examiner*—Kent Bell

(57) ABSTRACT

A new cultivar of *Gaura* plant named 'Bijou Butterflies' a perennial, characterized by dense compact, upright habit, dark purple stems, variegated green foliage with rose-purple margins, and red-purple flowers. In combination these traits set 'Bijou Butterflies' apart from all other existing varieties of *Gaura* known to the inventor.

2 Drawing Sheets

Genus: *Gaura.*
Species: *lindheimeri.*
Denomination: Bijou Butterflies.

BACKGROUND OF THE INVENTION

The present invention relates to a new and distinct variety of butterfly bush grown for use as an ornamental plant for the landscape. The new cultivar is known botanically as *Gaura lindheimeri* and will be referred to hereinafter by the cultivar name 'Bijou Butterflies'.

'Bijou Butterflies' is a spontaneous whole plant mutation that was selected by the inventor in the autumn of 2000. The parent plant is *Gaura lindheimeri* 'Crimson Butterflies' (U.S. Plant Pat. No. 13,189, Filed Apr. 18, 2001). The selection was conducted in a cultivated area of Wonga Park, Australia, and based on the criteria of leaf variegation and habit.

The closest comparison plant is *Gaura lindheimeri* 'Sunny Butterflies' (unpatented), which exhibits yellow-green stems and variegated green leaves with yellow-white margins. 'Bijou Butterflies' is distinguishable from 'Sunny Butterflies' by dark purple stems and variegated green leaves with rose-purple margins. 'Bijou Butterflies' is distinguishable from the parent plant 'Crimson Butterflies' by variegation of foliage. 'Crimson Butterflies' exhibits dark grey-purple leaves with no variegation.

'Bijou Butterflies' was first asexually propagated in 2000 by the inventor in a cultivated area of Wonga Park, Australia. The method of propagation used was vegetative stem cuttings. Cuttings were grown to rooted plugs, which were then transferred to 140 mm. containers, filled with pine bark based mix and maintained with controlled release fertilizers. Appropriate pest and disease treatments were applied as required. Propagation has continued through four successive generations since that time, showing characteristics of the new cultivar 'Bijou Butterflies' stable and reproduced true to type.

SUMMARY OF THE INVENTION

The following traits have been repeatedly observed and represent the distinguishing characteristics of the new plant 'Bijou Butterflies'. In combination these traits set 'Bijou Butterflies' apart from all other *Gaura* known to the inventor. 'Bijou Butterflies' has not been tested under all possible conditions and phenotypic differences may be observed with variations in environmental, climatic and cultural conditions, however, without any variance in genotype.

1. *Gaura* 'Bijou Butterflies' exhibits a compact dense upright habit.

2. *Gaura* 'Bijou Butterflies' exhibits dark purple stems.

3. *Gaura* 'Bijou Butterflies' exhibits variegated green leaves with rose-purple margins.

4. *Gaura* 'Bijou Butterflies' is propagated using vegetative stem cuttings.

5. *Gaura* 'Bijou Butterflies' exhibits red-purple flowers.

6. *Gaura* 'Bijou Butterflies' is hardy in USDA Zones 5–10.

7. *Gaura* 'Bijou Butterflies' is 30 cm. in height and 50 cm. in width at five months of age.

BRIEF DESCRIPTION OF THE DRAWINGS

The accompanying color drawings illustrate the overall appearance of the new cultivar 'Bijou Butterflies' showing the colors as true as it is reasonably possible to obtain in colored reproductions of this type. Colors in the drawings may differ from the color values cited in the detailed botanical description which accurately describe the actual colors of the new variety 'Bijou Butterflies'. The plant in the drawing is 5-months-old and was grown out-of-doors in Arroyo Grande, Calif. in a one-liter container then transplanted into the ground in full sun.

The drawing on sheet 1 illustrates plant habit and color from an upper side perspective.

The drawing on sheet 2 is a close-up view of the variegated foliage and a group of flowers.

Drawings were made using conventional techniques and although colors may appear different from actual colors due to light reflectance they are as accurate as possible by conventional photography.

BOTANICAL DESCRIPTION OF THE PLANT

The following is a detailed description of the new *Gaura* plant named 'Bijou Butterflies'. Data was collected in Arroyo Grande Calif. from 5-month-old plants that were grown in one-liter containers out-of-doors and transplanted into the ground. The color determinations are in accordance with The 2001 Royal Horticultural Society Colour Chart of The Royal Horticultural Society, London, England, except where general color terms of ordinary dictionary significance are used. The growing requirements are similar to other *Gaura*.

Botanical classification: *Gaura* 'Bijou Butterflies'.
Species: *lindheimeri*.
Commercial classification: Perennial.
Common name: Butterfly bush.
Use: Ornamental for container or landscape. Cultural requirements: Plant in well-drained moderately fertile soil in full sun.
Root system: Deep rooting makes the plant very drought tolerant.
Parentage: *Gaura* 'Bijou Butterflies' is a spontaneous whole plant mutation that resulted from the following parent plant:
- *Parent plant.*—*Gaura lindheimeri* 'Crimson Butterflies'.

Plant description:
- *Bloom period.*—Late spring to fall.
- *Plant habit.*—Upright, dense and compact.
- *Height.*—30 cm. in height at 5 months.
- *Width.*—50 cm. in width at 5 months.
- *Hardiness.*—USDA Zones 5–10.
- *Propagation.*—Propagation is accomplished using vegetative stem cuttings.
- *Time to develop roots.*—2–3 weeks are needed for initial cuttings to develop roots.
- *Crop time.*—4–6 months are needed to produce a finished 1-liter container.
- *Disease susceptibility and resistance.*—No known susceptibility to disease is known to the inventor.

Stem:
- *Shape.*—Cylindrical.
- *Stem color.*—187A.
- *Stem dimensions.*—12.5 cm. in length and 4 mm. in diameter.
- *Stem surface.*—Pubescent.
- *Internode length.*—0.75 cm. between nodes.
- *Branching habit.*—Open, branching from both base and stems.

Foliage:
- *Shape.*—Elongated oval.
- *Division.*—Simple.
- *Apex.*—Acute.
- *Base.*—Attenuate.
- *Venation pattern.*—Pinnate.
- *Vein color* (*adaxial surfaces*).—186C.
- *Vein color* (*abaxial surfaces*).—185B.
- *Margins.*—Entire.
- *Attachment.*—Sessile.
- *Arrangement.*—Alternate.
- *Leaf surface* (*adaxial and abaxial surfaces*).—Pubescent.
- *Leaf appearance.*—Irridescent.
- *Leaf dimensions.*—Leaf dimensions range from 1.75 cm. to 4.25 cm. in length and from 0.50 cm. to 1.25 cm. in width.
- *Leaf color* (*adaxial surface*).—Center is 147A and margin is 185B.
- *Leaf color* (*abaxial surface*).—Center is 148A and margin is 185B.
- *Fragrance.*—Grass-like.

Flowers:
- *Inflorescence.*—Spike.
- *Dimensions of inflorescence.*—9 cm. in length and 4 cm. in width.
- *Quantity of buds per peduncle.*—An average of 7–10.
- *Shape.*—Explanate.
- *Sexuality.*—Bisexual.
- *Flower dimensions.*—2.25 cm. in diameter and 2 cm. in length.
- *Persistent or self-cleaning.*—Self-cleaning.
- *Aspect.*—Facing outward.
- *Bud dimensions.*—2 mm. in width and 10 mm. in length.
- *Bud shape.*—Linear to narrow oval.
- *Bud color.*—187A.
- *Bud surface.*—Pubescent.
- *Color of pubescence.*—156D.
- *Bud apex.*—Acute.
- *Flower color.*—68B.
- *Calyx color.*—187C.
- *Sepals.*—Two in number.
- *Sepal color* (*abaxial and adaxial surfaces*).—187C.
- *Sepal apex.*—Acute.
- *Sepal base.*—Attenuate.
- *Sepal shape.*—Closest to linear.
- *Sepal margins.*—Entire.
- *Sepal surfaces* (*abaxial and adaxial surfaces*)—Pubescent.
- *Sepal dimensions.*—15 mm. in length and 3 mm. in diameter.
- *Petals.*—Four in number.
- *Petal color* (*adaxial and abaxial surfaces*).—68B.
- *Petal shape.*—Ovate.
- *Petal dimensions.*—15 mm. in length and 11 mm. in width.
- *Vein pattern.*—Pinnate.
- *Vein color* (*adaxial and abaxial surfaces*).—N66A.
- *Fused or unfused.*—Unfused.
- *Petal margin.*—Entire.
- *Petal apex.*—Rounded.
- *Petal base.*—Cuneate.
- *Petal surface.*—Glabrous.
- *Peduncle dimensions.*—15 cm. in length and 2 mm. in diameter.
- *Peduncle shape.*—Cylindrical.
- *Peduncle color.*—187A.
- *Peduncle surface.*—Pubescent.
- *Pedicel dimensions.*—9 mm. in length and 2 mm. in width.
- *Pedicel color.*—187A.
- *Pedicel surface.*—Puberulent.
- *Flower fragrance.*—None observed.

Reproductive organs:
- *Stamens.*—Eight in number.
- *Stamen color.*—N66B.
- *Stamen dimensions.*—9 mm. in length and 0.25 mm. in diameter.
- *Anther color.*—187A.
- *Anther dimensions.*—3 mm. in length and 0.50 mm. in width.
- *Quantity of pollen.*—Small amount.

*Color of pollen.*—155C.
*Pistil.*—One in number.
*Pistil dimensions.*—12 mm. in length and 0.50 mm. in width.
*Pistil color.*—N66B.
*Pistil shape.*—Filament.
*Style color.*—N66B.
*Stigma shape.*—Four lobed.
*Stigma color.*—N66B.
*Ovary position.*—Inferior.
*Ovary color.*—187A.
*Ovary shape.*—Linear to elongated oval.
*Ovary dimensions.*—6 mm. in length and 2 mm. in diameter.

Seed production: No seed production has been observed to date.

I claim:

1. A new and distinct cultivar of *Gaura* plant named 'Bijou Butterflies' as described and illustrated.

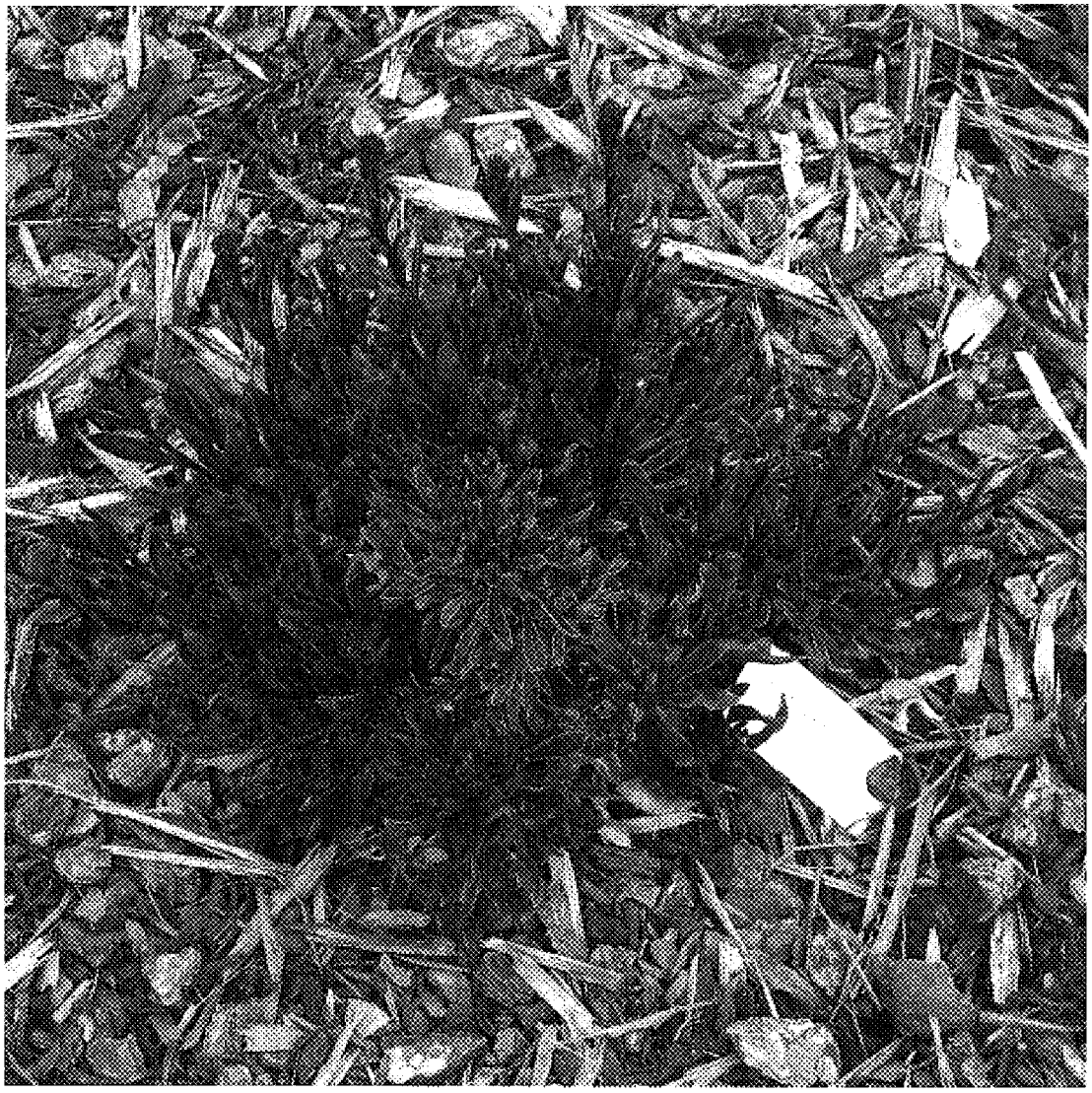

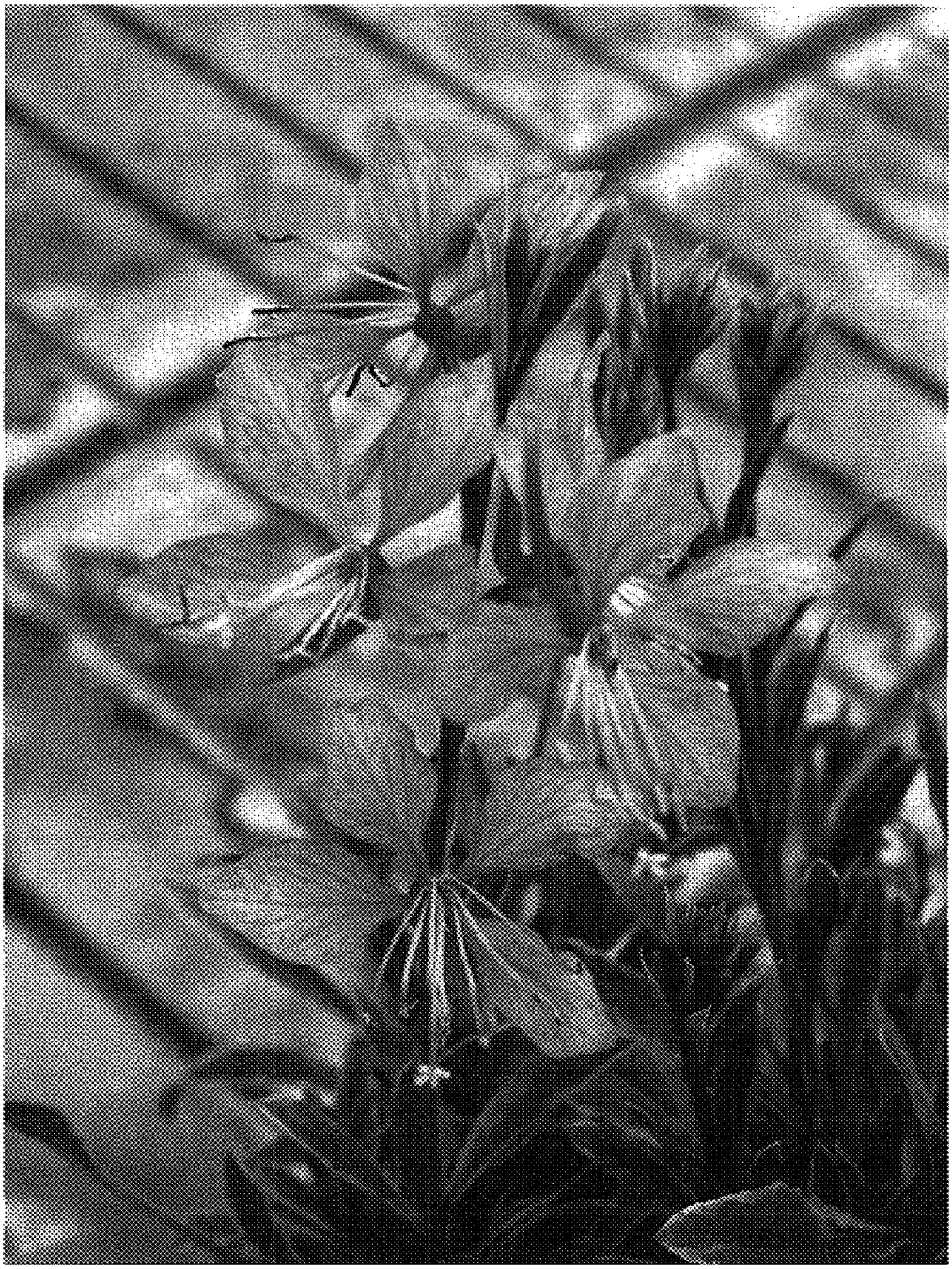

* * * * *